United States Patent
Hirao et al.

(10) Patent No.: US 6,888,025 B2
(45) Date of Patent: *May 3, 2005

(54) METHOD FOR ABSORBING ACRYLIC ACID AND METHOD FOR PURIFYING ACRYLIC ACID

(75) Inventors: Harunori Hirao, Hyogo (JP); Yoshitake Ishii, Hyogo (JP); Yukihiro Matsumoto, Hyogo (JP); Takeshi Nishimura, Hyogo (JP)

(73) Assignee: Nippon Shokubai, Co. Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/211,040

(22) Filed: Aug. 2, 2002

(65) Prior Publication Data

US 2003/0028052 A1 Feb. 6, 2003

Related U.S. Application Data

(63) Continuation-in-part of application No. 09/780,787, filed on Feb. 9, 2001, now Pat. No. 6,713,648.

(30) Foreign Application Priority Data

Feb. 14, 2000 (JP) ........................................ 2000-035107

(51) Int. Cl.[7] .............................................. C07C 51/42
(52) U.S. Cl. ...................................................... 562/600
(58) Field of Search ................................ 562/521, 532, 562/542, 545, 600

(56) References Cited

U.S. PATENT DOCUMENTS

| | | |
|---|---|---|
| 3,689,541 A | 9/1972 | Sennewald et al. |
| 3,868,417 A | 2/1975 | Duembgen et al. |
| 3,932,500 A | 1/1976 | Duembgen et al. |
| 4,110,370 A | 8/1978 | Engelbach et al. |
| 5,780,679 A | 7/1998 | Egly et al. |
| 5,817,865 A | 10/1998 | Machhammer et al. |
| 2001/0007043 A1 | 7/2001 | Machhammer et al. |

FOREIGN PATENT DOCUMENTS

| | | |
|---|---|---|
| DE | 198 14 375 | 10/1999 |
| DE | 198 36 367 | 2/2000 |
| EP | 0 982 289 | 3/2000 |

*Primary Examiner*—Paul A. Zucker
(74) *Attorney, Agent, or Firm*—Matthews, Collins, Shepherd & McKay, P.A.

(57) ABSTRACT

This invention concerns a method for absorbing acrylic acid, characterized by supplying an acrylic acid-containing reaction gas component obtained by the reaction of catalytic gas phase oxidation to an acrylic acid absorption column and advancing a high boiling inert hydrophobic organic liquid into counter-flow contact with said reaction gas in said acrylic acid absorption column with the mass flow rate of the organic liquid fixed in the range of 0.2–7.0 times the mass flow rate of the acrylic acid in the reaction gas thereby absorbing acrylic acid in said organic liquid and obtaining an acrylic acid-containing solution including a low boiling substance in the range of 0.7–7.5 wt % based on the weight of bottom liquid of absorption column.

5 Claims, 2 Drawing Sheets

Relationship of LB and LB/AA

FIG.1 Relationship of LB and LB/AA

FIG.2

METHOD FOR ABSORBING ACRYLIC ACID AND METHOD FOR PURIFYING ACRYLIC ACID

This is a continuation-in-part of Ser. No. 09/780,787 filed Feb. 9, 2001 now U.S. Pat. No. 6,713,648 in which the entire application is hereby incorporated by reference.

BACKGROUND OF THE INVENTION

1. Field of the Invention

This invention relates to a method for absorbing acrylic acid and a method for purifying acrylic acid, and more particularly to a method for the purification of acrylic acid which comprises absorbing acrylic acid by contact thereof at a specific ratio with a high boiling inert hydrophobic organic liquid and purifying the high boiling inert hydrophobic organic liquid containing acrylic acid at a specific concentration

2. Description of the Related Art

Such easily polymerizing substances as acrylic acid and methacrylic acid are raw materials for commercial manufacture and are chemical substances which are mass produced in a plant of a large scale. Since these compounds are generally produced through various steps of absorption and purification for the purpose of affording manufactured goods of high purity.

When propylene, propane, or acrolein, for example, is subjected to catalytic gas phase oxidation with a molecular oxygen-containing gas in the presence of an oxidizing catalyst, the oxidation generates such low boiling substances as acetic acid, lower aldehydes, and water and such high boiling substances as furfural and maleic anhydride as by products in addition to acrylic acid which is a target product. Thus, the mixed gas consequently obtained is guided to an acrylic acid absorption column and brought into contact therein with an absorbent to absorb and collect acrylic acid into the liquid, thereby obtaining a solution containing acrylic acid and other by-products and this solution is subjected to distillation, stripping, extraction, or crystallization to separate and purify acrylic acid and the product aimed at is obtained.

Since the absorption of acrylic acid from the acrylic acid-containing gas allows the acrylic acid to be absorbed in a high concentration, generally an absorbent having water as a main component is used for this absorption. Since this absorption can be attained in a high absorbing coefficient even at a comparatively high temperature in the range of 50–70° C., it is at an advantage in permitting a saving in the energy needed to cool the reaction gas which is generated at a high temperature in the neighborhood of 300° C.

The step for removing low boiling substances, however, requires a large volume of energy because it entails the necessity for separating water. Further, since the aqueous absorbent, while permitting easy absorption of acrylic acid, contains acrylic acid which is an easily polymerizing compound at a high concentration, it is liable to form acid dimer and polymer at the steps of absorption and purification. Particularly, since the water itself is a low boiling substance, the acrylic acid gains in concentration after from the step for separation and purification in a light ends cut column and tends to generate a polymer. Further, the low boiling substances are not easily separated in a purified form from acrylic acid and are possibly suffered to persist in relevant manufactured goods to the extent of degrading the purity thereof.

In contrast to the method which uses such a low boiling substance as water, for example, as the absorbent, a method for absorbing acrylic acid by using a high boiling inert hydrophobic organic liquid has been also known. This method is at an advantage in not suffering acrylic acid to gain in concentration till the final step for obtaining acrylic acid as a final product and repressing the amounts of dimer and polymer to be formed because the absorbent is a high boiling substance. Further, the separation of low boiling substances and the consequent purification of acrylic acid are attained far easier in this method than the method using the aqueous absorbent. Thus, the practice of purifying acrylic acid via an operation of recovery using a high boiling inert hydrophobic organic liquid prevails.

The official gazette of U.S. Pat. No. 4,110,370, for example, gives a description to the effect that, in a method for separating acrylic acid from a reaction gas mixture resulting from the catalytic gas phase oxidation of propylene by counter-flow absorption using a high boiling inert hydrophobic organic liquid, a mixture consisting of 73.5 wt. % of diphenyl ether and 26.5 wt. % of diphenyl is supplied at a flow rate of 450 kg per hour to an absorption column and the reaction gas arising from catalytic oxidation of propylene containing 3 vol. % of acrylic acid is supplied at a flow rate of 520 Nm3 per hour to the absorption column to absorb the acrylic acid. This operation as reduced to the standard condition equals supply of an absorbent at a feed rate of 450 kg per hour to 50.2 kg (520 Nm3×0.03×72.1 g/0.0224 m3) of acrylic acid. Thus, the ratio of the amount of the absorbent relative to acrylic acid of the operation disclosed in the official gazette is 450 kg/50.2 kg=about 9 times the amount of a high boiling inert hydrophobic organic liquid.

Then, the official gazette of U.S. Pat. No. 3,932,500 discloses in a working example cited therein the technique of absorbing acrylic acid by supplying 2692 N liters of a reaction gas containing 2.52 vol. % of acrylic acid to an absorption column and introducing thereto an absorbent consisting of 75 wt. % of diphenyl ether and 25 wt. % of diphenyl at a flow rate of 1.98 kg per hour. This operation as reduced to the standard condition equals supply of 1.98 kg per hour of the absorbent to 218 g (2692 N liters×0.0252× 72.1 g/22.4 liters) of acrylic acid. This time again, the ratio of the amount of the absorbent relative to acrylic acid of the operation disclosed in the official gazette is 1.98 kg/218 g=about 9 times the amount of a high boiling inert hydrophobic organic liquid.

The method disclosed in the official gazette of U.S. Pat. No. 5,780,679, likewise in a process of separating acrylic acid from the reaction gas mixture resulting from the catalytic gas phase oxidation of propylene and/or acrolein by counter-flow absorption using a high boiling inert hydrophobic organic liquid, absorbs acrylic acid by supplying an absorbent consisting of 57.2 weight % of diphenyl ether, 20.7 weight % of diphenyl, and 20 weight % of o-dimethyl phthalate at 52° C. at a flow rate of 160.8 kg per hour to 220.2 kg of a gas containing 13.5 weight % of acrylic acid at 204° C. The ratio of the amount of the absorbent relative to acrylic acid as disclosed in the official gazette is 160.8 kg/h/(220.2 kg/h×13.5/100)=5.4. This official gazette has a mention to the effect that in consequence of the absorption mentioned above, the bottoms of the acrylic acid absorption column have a low boiling substance concentration of 0.16 weight %.

When acrylic acid is absorbed by the use of a high boiling inert hydrophobic organic liquid as described above, since the organic liquid manifests an inferior absorbing ability to acrylic acid, it is ordinary to use the organic liquid in a large volume in an effort to repress the loss of acrylic acid through the top of the acrylic acid absorption column. In the conventional techniques, the ratios of the amount of an absorbent relative to acrylic acid have been invariably not less than 5.4 as described above.

Since the high boiling inert hydrophobic organic liquid has a high price, the necessity for reusing the organic liquid which has been used in the process for purifying the produced acrylic acid is markedly high as compared with the aqueous absorbent. In this case, since the repurification of the used organic liquid must avoid inducing excess concentration of the high boiling substance contained therein, the reuse of interest has its own limit. Further, the use of the organic liquid in a large amount inevitably entails the problem of adding to utilities for transfer and enlarging devices and pipes used for the transfer.

Moreover, the use of the high boiling inert, hydrophobic organic liquid particularly in a large amount as an absorbent entails an addition to the amount of absorption of the low boiling substance which is difficult of separation from acrylic acid. Since acrylic acid and the low boiling substance are separated only with difficulty in the distillation column, the low boiling substance possibly persists in the crude acrylic acid to be produced. For the purpose of decreasing the mass of the low boiling substance in the crude acrylic acid, therefore, it becomes necessary to subject the crude acrylic acid further to a treatment for purification intended to separate the low boiling substance and, to increase the reflux ratio during the course of the purification.

SUMMARY OF THE INVENTION

The present inventor has pursued an elaborate study on the step for absorption of an acrylic acid-containing gas and the step for separation by distillation of a low boiling substance which have been in vogue heretofore. He has consequently found that the absorbing coefficient of a low boiling substance is lowered and a high boiling inert hydrophobic organic liquid having a high acrylic acid concentration is obtained while the absorbing coefficient of acrylic acid is kept intact by decreasing the amount of an absorbent in an acrylic acid absorption column and, at the same time, lowering the temperature of the top of the column. Further, what surprises the inventor is the fact that the acrylic acid-containing high boiling inert hydrophobic organic liquid obtained in consequence of this absorption exceptionally excels in the ratio of separation of a low boiling substance. Thus, by the use of the high boiling inert hydrophobic organic liquid of a low capacity which excels not only in economy but also in the effect of separation of a low boiling substance, the product of acrylic acid is enabled to be manufactured easily with high purity. The task imposed on this invention is accomplished by the following item.

A method for absorbing acrylic acid, characterized by supplying an acrylic acid-containing reaction gas component obtained by the reaction of catalytic gas phase oxidation to an acrylic acid absorption column and advancing a high boiling inert hydrophobic organic liquid into counter-flow contact with said reaction gas in said acrylic acid absorption column with the mass flow rate of the organic liquid fixed in the range of 0.2–7.0 times the mass flow rate of the acrylic acid in the reaction gas thereby absorbing acrylic acid in said organic liquid and obtaining an acrylic acid-containing solution including a low boiling substance in the range of 0.7–7.5 wt % based on the weight of bottom liquid of absorption column.

By this invention, in the absorption of an acrylic acid-containing gas resulting from the reaction of catalytic gas phase oxidation by the use of a high boiling inert hydrophobic organic liquid, by using the high boiling inert hydrophobic organic liquid in an amount 0.2–7.0 times the mass flow rate of the gas, it is made possible to obtain bottoms of an absorption column containing a low boiling substance at a low concentration and, by effecting the purification with the bottoms, it is enabled to obtain a product of acrylic acid containing a low boiling substance at a low concentration.

BRIEF DESCRIPTION OF THE DRAWINGS

FIG. 1 is a diagram showing the ratio of a low boiling substance to acrylic acid to be found when acrylic acid is absorbed and a low boiling substance is separated for varying ratio of the amount of an absorbent relative to an acrylic acid-containing gas. In the diagram, the ratios of a low boiling substance (acetic acid, acrolein, water, etc) to acrylic acid in the bottoms of an acrylic acid absorption column found in an operation of supplying to the acrylic acid absorption column a reaction gas (AA: 7.15 vol %, LB: 14.6 vol %) resulting from the reaction of catalytic gas phase oxidation of propylene and adjusting the ratio of amount of absorbent/gas by varying the amount of the high boiling inert hydrophobic organic liquid (composition: 73.5 weight % of diphenyl ether and 26.5 weight % of diphenyl) are indicated with filled circles (●) and the amounts (weight ppm) of a low boiling substance relative to acrylic acid in the bottoms of a light ends cut column found in an operation of distilling the bottoms containing acrylic acid at the aforementioned concentration are indicated with filled triangles (▲).

DESCRIPTION OF THE PREFERRED EMBODIMENTS

This invention concerns a method for absorbing acrylic acid, characterized by supplying an acrylic acid-containing reaction gas component obtained by the reaction of catalytic gas phase oxidation to an acrylic acid absorption column and advancing a high boiling inert hydrophobic organic liquid into counter-flow contact with said reaction gas in said acrylic acid absorption column with the mass flow rate of the organic liquid fixed in the range of 0.2–7.0 times the mass flow rate of the acrylic acid in the reaction gas thereby absorbing acrylic acid in said organic liquid and obtaining an acrylic acid-containing solution including a low boiling substance in the range of 0.7–7.5 wt % based on the weight of bottom liquid of absorption column. The term "mass flow rate of an acrylic acid in a reaction gas" as used herein refers to weight of an acrylic acid in the reaction gas to be supplied into an acrylic acid absorption column per an hour. Similarly, the term "mass flow rate of a high boiling inert hydrophobic organic liquid" refers to a weight of the organic liquid to be supplied into an acrylic acid absorption column per an hour. Moreover, the term "purification" as used in the specification hereof embraces distillation and stripping. The term "distillation" as used herein refers to a method for heating a given solution till the boiling point thereof and separating the volatile component contained therein and the term "stripping" as used herein refers to a method for supplying a stripping gas thereby migrating the gas or the vapor dissolved in the solution to the gas phase. Now, this invention will be described in detail below.

The high boiling inert hydrophobic organic liquid has a low ability to absorb acrylic acid as compared with the aqueous absorbent. Thus, in the absorption of the acrylic acid-containing gas resulting from the reaction of catalytic gas phase oxidation by the use of the organic liquid, it has been ordinary for the sake of effective absorption of acrylic acid emanating from the top of an acrylic acid absorption column to use the absorbent in an amount exceeding 5.4 times the mass flow rate of the acrylic acid in the reaction gas. Since the high boiling inert hydrophobic organic liquid is expensive, however, the necessity for reusing this organic liquid is great and particularly the decrease in the amount of the absorbent, if successful, results in decreasing the cost for transfer and proves economically advantageous. An experiment conducted on the absorption of acrylic acid, with the amount of supply of a high boiling inert hydrophobic organic liquid to an acrylic acid-containing gas varied during the process of the absorption of acrylic acid, has revealed the relation between the acrylic acid absorbed by the high boiling inert hydrophobic organic liquid and a low boiling substance as shown in Table 1 and FIG. 1. As used in Table 1 and FIG. 1, AA stands for acrylic acid, LB for a low boiling substance, and the amount of absorbent/gas for the ratio of the mass flow rate of the absorbent relative to the acrylic acid in the reaction gas.

TABLE 1

Figure 1:
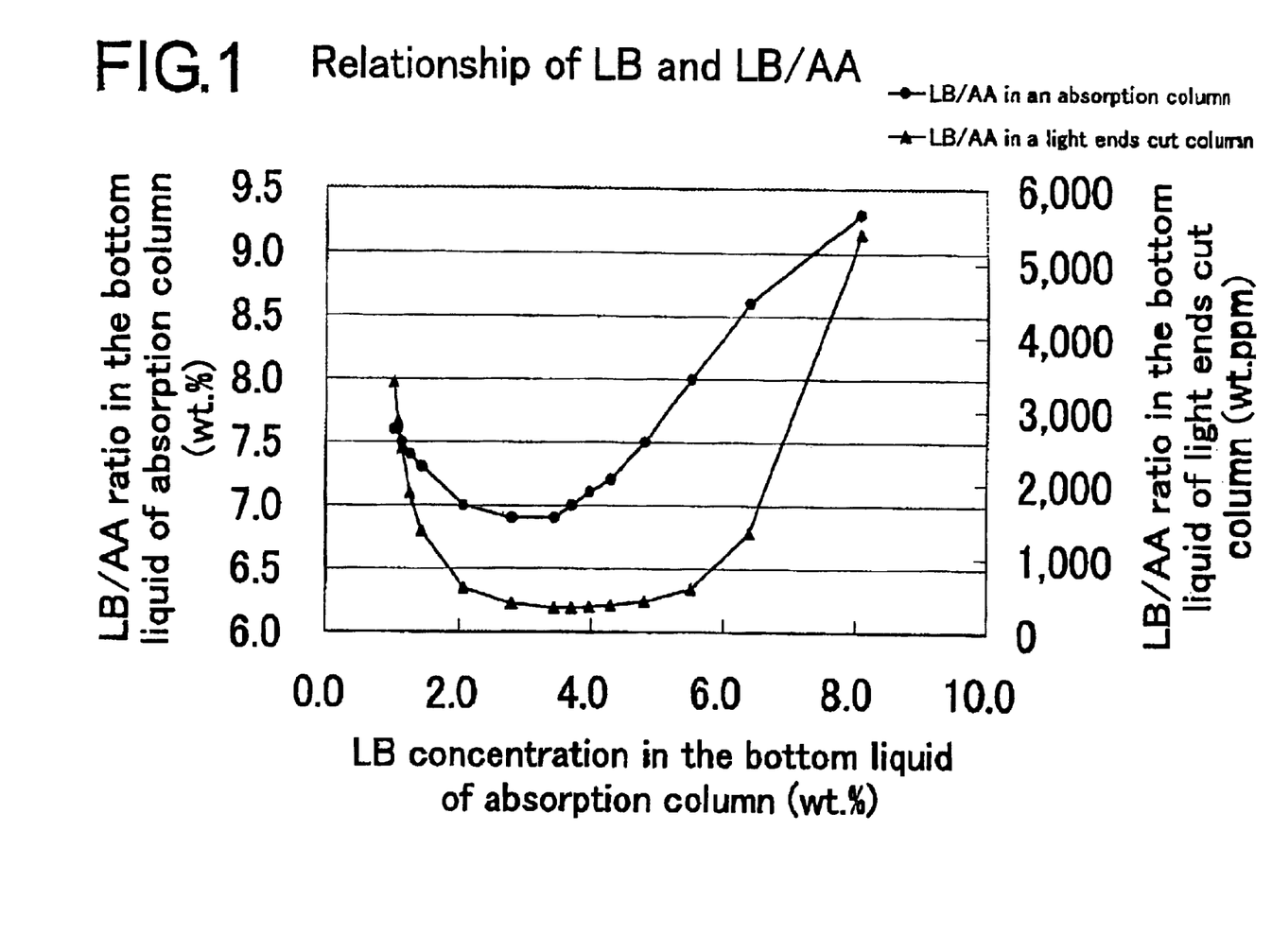

| Amount of absorbent/ gas | Bottoms liquid of acrylic acid absorption column | | | Bottoms liquid of light ends cut column | |
|---|---|---|---|---|---|
| | AA conc. (weight %) | LB conc. (weight %) | LB/AA ratio (weight %) (X) | LB/AA ratio (weight ppm) (Y) | Ratio of LB separation (X − Y)/X |
| 6.7 | 13.1 | 1.00 | 7.6 | 3380 | 0.956 |
| 6.1 | 14.1 | 1.07 | 7.6 | 2860 | 0.962 |
| 5.6 | 15.0 | 1.13 | 7.5 | 2480 | 0.967 |
| 4.8 | 17.0 | 1.26 | 7.4 | 1880 | 0.975 |
| 4.0 | 19.7 | 1.44 | 7.3 | 1360 | 0.982 |
| 2.3 | 29.6 | 2.07 | 7.0 | 600 | 0.992 |
| 1.4 | 40.6 | 2.80 | 6.9 | 390 | 0.995 |
| 0.9 | 49.8 | 3.44 | 6.9 | 330 | 0.995 |
| 0.8 | 52.8 | 3.70 | 7.0 | 330 | 0.995 |
| 0.7 | 56.1 | 3.98 | 7.1 | 340 | 0.995 |
| 0.6 | 59.9 | 4.31 | 7.2 | 360 | 0.995 |
| 0.5 | 64.1 | 4.81 | 7.5 | 410 | 0.995 |
| 0.3 | 68.9 | 5.51 | 8.0 | 580 | 0.993 |
| 0.2 | 74.4 | 6.40 | 8.6 | 1340 | 0.985 |
| 0.1 | 87.1 | 8.10 | 9.3 | 5400 | 0.942 |

When the amounts of the absorbent and the gas in an acrylic acid absorption column are varied, the variations cause the concentration of acrylic acid and the concentration of a low boiling substance in the bottoms liquid of an acrylic acid absorption column to vary proportionately. It follows that the ratio in weight % of the low boiling substance to the acrylic acid can be calculated at a varying low boiling substance concentration of the bottoms liquid of the acrylic acid absorption column (Table 1 refers). The filled circles (●) in FIG. 1 depict this relation. It is noted from the data of interest that the separation between the acrylic acid and the low boiling substance is such that the efficiency of this separation increases in accordance as the LB/AA ratio decreases and that the LB/AA ratio mentioned above is low particularly when the concentration of low boiling substance in the bottoms of the acrylic acid absorption column is in the range of 1.5–4.5 weight %. The data "ratio of LB separation [(X−Y)/X]" shown in Table 1 represent the results obtained by supplying the bottoms of the acrylic acid absorption column to the light ends cut column, separating the low boiling substance therein, and calculating the ratio of separation of the low boiling substance.

What is found from these results is the fact that the concentration of the low boiling substance in the bottoms of the acrylic acid absorption column increases in inverse proportion to the decrease in the amount of the absorbent to be used and that the concentration of the low boiling substance relative to the amount of acrylic acid in the bottoms shows the lowest value of 6.9 when the ratio of amount of absorbent/gas is in the range of 1.4 to 0.9 and increases before and after this range. That is, when the ratio of amount of absorbent/gas is varied, this variation brings a difference between the absorbing coefficient of the low boiling substance and the absorbing coefficient of acrylic acid. By effecting the absorption with the absorbent used in a specific ratio of amount, therefore, it is made possible to obtain the high boiling inert hydrophobic organic liquid absorbing a low boiling substance in a small amount and containing acrylic acid at a high concentration. Moreover, the ratio of separation of the low-boiling substance is increased when the low boiling substance is separated by using the bottoms liquid, which has the low LB/AA ratio, of an acrylic acid absorption column in a light ends cut column. For example, the ratio of LB separation in the light ends cut column shows a peak top of 0.995 when the concentration of low boiling substance in the bottoms of the acrylic acid absorption column supplied to the light ends cut column is in the range of 2.80–4.81 weight % and this ratio of LB separation in the light ends cut column gradually decreases before and after the peak top in accordance with increase of the LB/AA ratio in the bottoms of the acrylic acid absorption column. This fact indicates that the separation of the low boiling substance is varied by the LB/AA ratio in the bottoms of the acrylic acid absorption column.

What should be particularly noted here is the fact that even when the LB/AA ratio in the bottoms of the acrylic acid absorption column is fixed, the ratio of LB separation in the light ends cut column increases in accordance as the concentration of LB increases. This fact can be easily confirmed by the observation that when the LB/AA ratio in the bottoms of the acrylic acid absorption column is fixed at 7.5 and the LB concentration in the bottoms of the acrylic acid absorption column is set at 1.13 and 4.81 weight %, the ratio of LB separation in the light ends cut column becomes 0.967 and 0.995 respectively. From these results, it is inferred that the use of an acrylic acid solution having a low boiling substance concentration in the range of 0.7–7.5 weight % facilitates the separation of the low boiling substance and permits acrylic acid to be purified to a high concentration.

The characteristic feature of this invention can be summarized as follows by comparison with the conventional technique using a high boiling inert hydrophobic organic liquid. It has been ordinary for the concentration of low boiling substance to fall below 0.7 weight % and the mass flow rate of the absorbent in the acrylic acid absorption column has exceeded 5.4 times the mass flow rate of acrylic acid in the reaction gas. In this invention, however, by decreasing the amount of the absorbent, it is made possible to increase the concentration of acrylic acid and decrease the amount of the low boiling substance to be absorbed while keeping the absorbing coefficient of acrylic acid intact. Moreover, when the low boiling substance is removed by distillation from the solution which has a high low boiling substance concentration and a low LB/AA ratio, the efficiency of separation in the light ends cut column is increased. The present invention, therefore, permits the product of acrylic acid to be manufactured easily in high purity. Further, by using the acrylic acid-containing organic liquid of high concentration, it is enabled to secure the economy of energy. Since the absolute amount of substances other than acrylic acid is decreased, the attempt to repress the amount of utilities spent for transfer and miniaturize the device used for the transfer can be fulfilled. This relation between the acrylic acid and the low boiling substance in the acrylic acid absorption column and the light ends cut column has never been known to the art and has been discovered for the first time by the present inventor. The term "low boiling substance" as used in this invention refers to a substance which has a lower boiling point than acrylic acid in the standard condition. As concrete examples of the low boiling substance, formic acid, acetic acid, acrolein, formaldehyde, acetaldehyde, and water may be cited. The term "high boiling substance" as used herein refers to a substance which has a higher boiling point than acrylic acid in the standard condition. As concrete examples of the high boiling substance, furfural, maleic anhydride, acrylic acid oligomer, and a high boiling solvent may be cited. Then, the term "non-condensing gas" as used herein refers to a substance which is in a gaseous state under the standard condition. As concrete examples of the non-condensing gas, nitrogen, oxygen, air, propylene, propane, carbon monoxide, and carbon dioxide may be cited.

This invention has originated in the discovery that the amount of a low boiling substance in the product of acrylic acid can be decreased by using the organic liquid containing low boiling substance at a concentration in the range of 0.7–7.5 weight %. Generally, the high boiling inert hydrophobic organic liquid which contains the reaction gas resulting from the reaction of catalytic gas phase oxidation in such an amount that the low boiling substance concentration falls in the range of 0.7–7.5 weight %, preferably in the range of 0.75–6.4 weight %, and particularly in the range of 1.2–6.4 weight %, can be used. If the low boiling substance concentration falls short of 0.7 weight %, the shortage will be at a disadvantage in heightening the LB/AA ratio in the bottoms of the light ends cut column obtained by the use of the relevant organic liquid, necessitating excessively the energy necessary for the removal of the high boiling inert hydrophobic organic liquid, and entailing an increase in the utilities for transfer and addition to the sizes of devices and pipes used for the transfer. Conversely, if the low boiling substance concentration exceeds 7.5 weight %, the excess will be at a disadvantage in heightening the LB/AA ratio in the bottoms of the light ends cut column produced by using the relevant organic liquid.

From the viewpoint of exalting the efficiency of separation of the low boiling substance, it is advantageous to purify the organic liquid at least till the low boiling substance content reaches a level in the range of 0.7–7.5 weight % and the ratio, in weight %, of the low boiling substance relative to the acrylic acid reaches a level in the range of 5.0–10.0 weight %, preferably in the range of 6.0–9.0 weight %, and particularly in the range of 6.5–8.0 weight %. The reason for setting these specific ranges is that the ratio of separation of the low boiling substance is variable with the mass of the low boiling substance relative to the acrylic acid and that, when the feed liquid satisfying such specific ranges is distilled, the acrylic acid and the low boiling substance can be separated with exceptionally high efficiency.

The method for preparing the acrylic acid-containing organic liquid of such a quality as described above has no limitation. It is nevertheless advantageous to use what is obtained by advancing the reaction gas resulting from the reaction of catalytic gas phase oxidation in the acrylic acid absorption column into counter-flow contact with the high boiling inert hydrophobic organic liquid at a rate in the range of 0.2–7.0 times, preferably 0.2–6.7 times, more preferably 0.2–4.8 times the mass flow rate of the organic liquid and effecting absorption of the reaction gas in the organic liquid. The reason for specifying the range is that the amount of the low boiling substance to be absorbed varies with the amount of the absorbent as described above. If the ratio of the mass flow rate mentioned above falls short of 0.2 times the mass flow rate, the shortage will be at a disadvantage in increasing the amount of the low boiling substance to be entrained in the bottom of the acrylic acid absorption column and, at the same time, rendering the setting of the acrylic acid concentration at a level in the range mentioned above difficult to achieve. Conversely, if the ratio exceeds 7.0 times the mass flow rate, the excess will be at a disadvantage in rendering it difficult to secure the range of acrylic acid concentration excelling in purifying by separation of the low boiling substance and requiring energy necessary for the separation of the high boiling inert hydrophobic organic liquid as well. Further, the use of the organic liquid in a large amount forms a cause for increasing the utilities for transfer and enlarging the device and the pipe for the transfer.

Now, this invention will be described below with the aid of a process diagram (FIG. 2) illustrating one example of the process for purification of acrylic acid.

Figure 2:
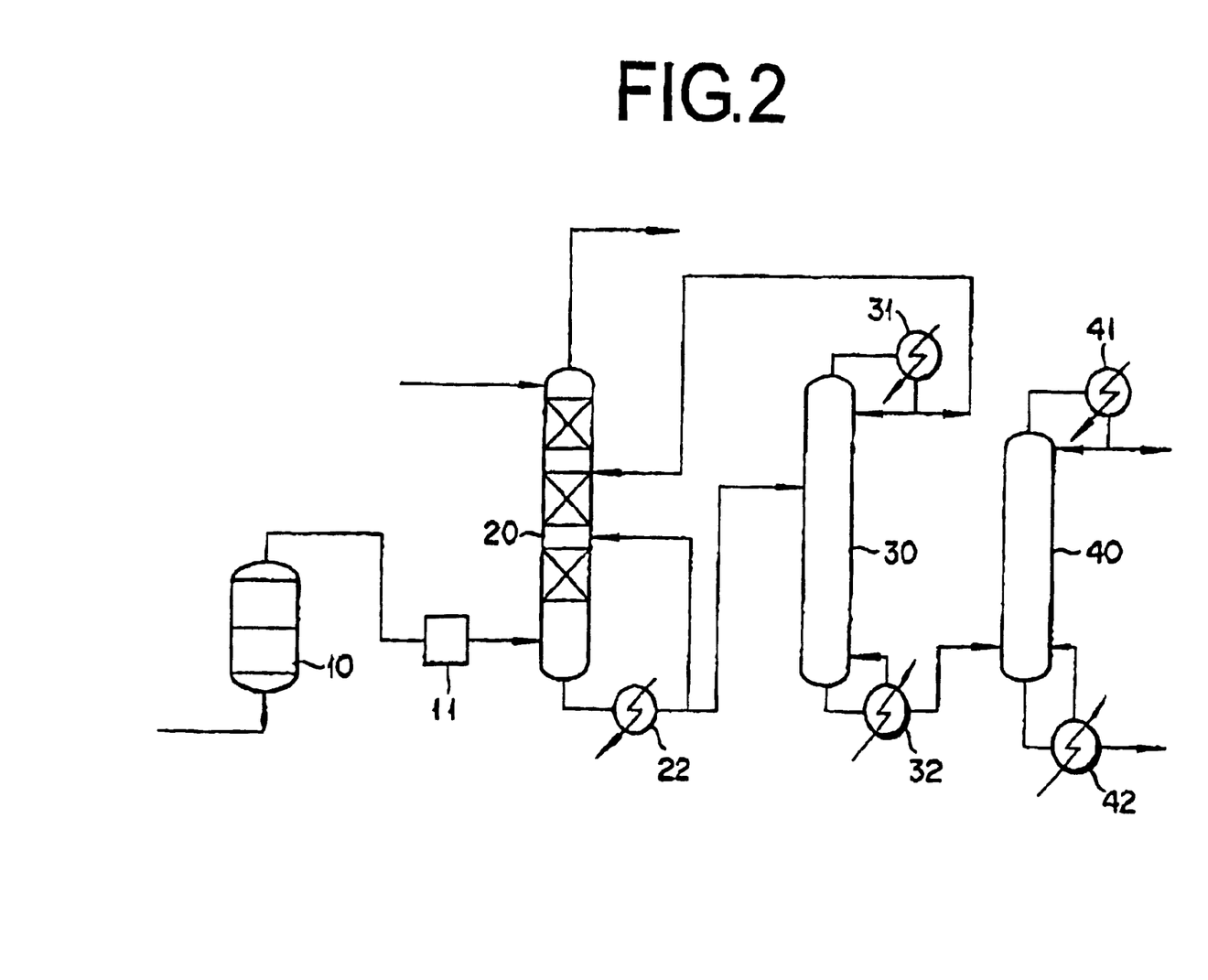
FIG. 2 is a schematic diagram illustrating a preferred mode of embodying the method of purification according to this invention.

With reference to FIG. 2, 10 stands for a reactor for catalytic gas phase oxidation, 11 and 22 each for a heat exchanger, 20 for an acrylic acid absorption column, 30 for a light ends cut column, 31 and 41 each for a condenser, 32 for a reboiler, 40 for a heavy ends cut column, and 42 for a reboiler. The raw material gas is supplied to the reactor (10) for catalytic gas phase oxidation, and acrylic acid in the reacted gas is absorbed in the acrylic acid absorption column (20) by using a high boiling inert hydrophobic organic liquid, and then purified by passage through the light ends cut column (30) and the heavy ends cut column (40), with the result that the product of acrylic acid will be obtained through the top of the heavy ends cut column (40).

When the acrylic acid is absorbed by using the high boiling inert hydrophobic organic liquid, since the high boiling inert hydrophobic organic liquid is expelled very rarely by the distillation in the separation columns (30, 40), "the absolute amount of the high boiling inert hydrophobic organic liquid" in the acrylic acid-containing organic liquid of the bottoms of the acrylic acid absorption column (20) is characterized by being sparingly varied during the supply thereof to the light ends cut column (30) and the heavy ends cut column (40). The low boiling substance as impurities are removed during the step of purification in this while. When the low boiling substance concentration in the bottoms of the acryl acid absorption column (20) reaches 3.0 weight %, therefore, the low boiling substance concentration will not exceed 3.0 weight % during the supply of the bottoms to the light ends cut column (30) and the heavy ends cut column (40).

Even when the bottoms of an absorption column having a low boiling substance concentration of 0.2 weight % are obtained and purified by the conventional method, the low boiling substance concentration in the acrylic acid-containing solution supplied to the purification column at the final stage of the process of purification will not exceed 0.2 weight %. The characteristic feature of this invention which resides in supplying the high boiling inert hydrophobic organic liquid having a low boiling substance concentration in the range of 0.7–7.5 weight % to the purification column will not occur.

First, the raw material gas is supplied to the reactor (10) for catalytic gas phase oxidation and subjected therein to the reaction of catalytic gas phase oxidation to form an acrylic acid-containing gas. This reaction of catalytic gas phase oxidation does not need to be particularly discriminated but is only required to be capable of forming acrylic acid with a catalyst for gas phase oxidation. To be specific, propylene, propane, or acrolein and a molecular oxygen-containing gas and an inert gas are supplied in their respectively prescribed amounts to a reactor such as a shell-and-tube reactor in the presence of an oxidizing catalyst to effect the reaction of catalytic gas phase oxidation. For example, acrolein is formed when propylene is used and then acrylic acid is obtained by further subjecting the acrolein to the reaction of catalytic gas phase oxidation. The process of reaction contemplated by this invention makes no discrimination between the one-step mode for performing the reaction in one reactor and the two-step mode for performing the reaction in two different reactors. As regards the reaction conditions such as the raw material, oxidizing catalyst, inert gas, oxygen gas, and reaction temperature to be used herein, the conditions for the known process for the reaction of acrylic acid are invariably applicable hereto.

For example, any one member or a mixture of two or more members selected from among propylene, propane, and acrolein may be used as the raw material gas. These raw material components account for a proportion in the range of 1–15 vol. % of the raw material gas to be supplied to the reactor. Further, the raw material gas contains the molecular oxygen for effecting the reaction of oxidization at a ratio in the range of 1–3 relative to the raw material and the inert gas such as carbon dioxide or steam at a ratio accounting for the balance.

Though the reactor for performing the reaction of catalytic gas phase oxidation does not need to be particularly restricted, the shell-and-tube type reactor can be used advantageously in respect that it excels in the efficiency of reaction.

This invention, in producing acrylic acid by the two-stage reaction of catalytic gas phase oxidation of a propylene-containing gas, for example, can use as the former-stage catalyst the oxidizing catalyst which is ordinarily used in the production of acrolein by the reaction of catalytic gas phase oxidation of a raw material gas containing propylene. The latter-stage catalyst does not need to particularly discriminated. For example, the oxidizing catalyst which is ordinarily used in producing acrylic acid by the gas phase oxidation of a reaction gas mainly containing acrolein as obtained in the former stage of the two-stage method for catalytic gas phase oxidation can be used.

Generally, the acrylic acid-containing gas which is obtained by the reaction of catalytic gas phase oxidation has a temperature in the range of 200–350° C. Preferably it is cooled to a temperature in the range of 100–300° C., especially in the range of 130–270° C., before it is supplied to the acrylic acid absorption column. As the heat exchanger (11) used for this cooling, any of the heat exchangers known to the art can be used. This cooling is required to ensure the temperature of the reaction gas mixture being not lowered below the dew point thereof. Of course this cooling is not required when the temperature of the reaction gas is already in the proper range.

The composition of the reaction gas which is obtained by the reaction of catalytic gas phase oxidation generally comprises 2–9 vol. % of acrylic acid, 0.1–1 vol. % of acetic acid and aldehyde as the low boiling substances excluding steam, 0.01–1 vol. % of furfural and maleic anhydride as high boiling substances, and the balance of non-condensing gas and steam.

This invention can use the reaction gas composition of any of the known reactions for catalytic gas phase oxidation.

The acrylic acid concentration in the reaction gas is preferably in the range of 3–9 vol. %, more preferably in the range of 4–9 vol. %, and particularly in the range of 5–9 vol. %. The reason for this range is that if the acrylic acid concentration is short of 3 vol. %, the shortage will lower the yield of the product. The reaction gas having an acrylic acid concentration exceeding 9 vol. % will be obtained only with difficulty and this excess of the acrylic acid concentration will abruptly increase the amount of by-products other than acrylic acid and will consequently render the subsequent purification difficult to attain. The production of the reaction gas having an acrylic acid concentration in the specified range can be easily accomplished by properly selecting the amount of the raw material gas supplied per unit time to the reactor for catalytic gas phase oxidation and the kind of the catalyst to be used for the reaction of catalytic gas phase oxidation.

This invention supplies the acrylic acid-containing gas to the acrylic acid absorption column (20) and absorbs it by using the high boiling inert hydrophobic organic liquid therein.

As the high boiling inert hydrophobic organic liquid which can be used in the acrylic acid absorption column, any of the known absorbents can be adopted. As concrete examples of the high boiling inert hydrophobic organic liquid, a mixture consisting of 70–75 weight % of diphenyl ether and 25–30 weight % of diphenyl and a mixture obtained by adding 0.1–25 weight % of o-diphenyl phthalate to a mixture consisting of 70–75 weight % of diphenyl ether and 25–30 weight % of diphenyl may be cited.

The temperature of the top of the column for the absorption column is preferred to be low for the purpose of exalting the absorbing coefficient of acrylic acid. The high boiling inert hydrophobic organic liquid absorbs acrylic acid at a lower ratio than the absorbent which has water as a main component. Thus, the temperature of the top of the acrylic acid absorption column is lowered by the use of a cooling device annexed to the absorption column to a level preferably in the range of 20–70° C., more preferably in the range of 20–60° C., and particularly in the range of 30–60° C. If this temperature falls short of 20° C., the shortage will be at a disadvantage in causing the absorbent to suffer growth in viscosity and inducing degradation of the stage efficiency of the acrylic acid absorption column owing to the loss of pressure in the acrylic acid absorption column and the deterioration of the distribution of the liquid and, moreover, necessitating an undue cooling energy. Conversely, if this temperature exceeds 70° C., the excess will be at a disadvantage in lowering the absorbing coefficient of acrylic acid.

The absorbent, for the purpose of preventing such polymerizing substance as acrylic acid from undergoing polymerization, is preferred to contain at least one compound selected from the group consisting of N-oxyl compounds, phenol compounds, manganese salts such as manganese acetate, copper salts of dialkyldithiocarbamic acid such as copper dibutylthiocarbamate, nitroso compounds and amine compounds, or one or more the compounds plus phenothiazine. The method of absorption according to this invention brings a higher acrylic acid concentration in the bottoms of the acrylic acid absorption column than when the absorption of acrylic acid is effected by using the conventional high boiling inert hydrophobic organic liquid. Since this method is liable to generate a polymer, it requires addition of a polymerization inhibitor for the sake of preventing such polymerization.

The N-oxyl compounds to be effectively used herein do not need to be particularly restricted. As concrete examples of the N-oxy compounds which are preferably used because of their ability to afford a satisfactory effect in preventing polymerization, 2,2,6,6-tetramethyl piperidinoxyl, 4-hydroxy-2,2,6,6-tetramethyl piperidinoxyl, and 4,4',4"-tris-(2,2,6,6-tetramethyl piperidinoxyl) phosphite may be cited. These N-oxyl compounds may be used either singly or in the form of a mixture of two or more members.

The phenol compounds which are effectively used herein include hydroquinone, p-methoxyphenol (methoquinone), cresol, and t-butyl catechol. Optionally, these phenol compounds may be used in the form of a combination of two or more members.

As concrete examples of the manganese salts which are effectively used herein, manganese formate, manganese acetate, manganese octanoate, manganese naphthenate, manganese permanganate, and manganese salts of ethylenediamine tetraacetic acid may be cited. Optionally, these manganese salts may be used in the form of a combination of two or more members.

The alkyl group in the copper salts of dialkyl dithiocarbamic acid is one member selected from the group consisting of methyl, ethyl, propyl, and butyl. The two alkyls of "dialkyl" may be identical or not identical. As a concrete example of the copper salt of dialkyl dithiocarbamic acid, copper diphenyl dithiocarbamate may be cited. The copper salts of dialkyl dithiocarbamic acid may be used in the form of a combination of two members. As concrete examples of the nitroso compounds, p-nitrosophenol, N-nitrosodiphenyl amine, and ammonium salts of N-nitrosophenyl hydroxyamine may be cited. Optionally, these nitroso compounds may be used in the form of a combination of two or more members. As concrete examples of the amine compounds, diphenyl amine, p-phenylene diamine, and p-aminophenol may be cited. Optionally, these amine compounds may be used in the form of a combination of two or more members.

This invention prefers the absorbent of interest to contain one or more compounds selected from the group consisting of N-oxyl compounds, phenol compounds, manganese salts, copper salts of dialkyl dithiocarbamic acid, nitroso compounds and amine compounds, or one or more such compounds plus phenothiazine. Of course, the combined system using three or more components, i.e. two or more compounds from the six kinds mentioned above plus a phenothiazine compound, obtains an effect of preventing polymerization to a level equal to or even better than the two component system.

The amount of the polymerization inhibitor to be used does not need to be particularly limited but is only required to be properly adjusted, depending on the relevant operating conditions. It is, however, preferable to set the total amount of the polymerization inhibitor to be used at a ratio in the range of 3–650 weight ppm based on the weight of the acrylic acid in the reaction gas to be absorbed. Concerning the preferred amounts of the individual polymerization inhibitors to be used, the preferred amount of a N-oxyl compound is in the range of 1–100 weight ppm based on the weight of the acrylic acid in the reaction gas, that of a manganese salt or a copper salt is in the range of 1–50 weight ppm based on the weight of the acrylic acid in the reaction gas, and that of a copper salt of dialkyl dithiocarbamic acid, an amine compound, or a nitroso compound is in the range of 1–500 weight ppm.

The site for supply of the polymerization inhibitor does not need to be particularly restricted. Preferably, however, the supply is made through the top of the absorption column. When the polymerization inhibitor is supplied after it has been mixed in advance with the solvent, this supply is effective in uniformly distributing the polymerization inhibitor in the absorption column. It is preferable to use an absorbent or acrylic acid as the solvent and it is economical to reclaim the absorbent separated in the purification column.

The addition of the polymerization inhibitor can be effected during the process for purification of acrylic acid and during the storage of a monomer. It is commended to make the addition in the amount specified above relative to the amount of the vapor of acrylic acid to be evaporated in the case of the addition during the purification or to the weight of the liquid of acrylic acid and an ester thereof in the case of the addition during the storage of a monomer. The term "amount of the vapor to be evaporated" means the total amount of the vapor of the monomer generated. The total amount of the vapor of the monomer can be easily found by calculation and the numeral thereof constitutes itself the important factor in deciding the standard for injection of the polymerization inhibitor.

In the method of purification according to this invention, the bottoms of the column for absorption of acrylic acid can be used in their unmodified form for purification in the subsequent step for purification. For the purpose of adjusting the operating conditions of the acrylic acid absorption column so as to set the low boiling substance concentration in the range of 0.7–7.5 weight %, it suffices to adjust the pressure, temperature, and amount of the absorbent. Particularly, in this invention, the absorbent is brought into counter-flow contact with the reaction gas in an amount preferably in the range of 0.2–7.0 times the mass flow rate of the organic liquid and effecting absorption of the reaction gas in the organic liquid and obtaining an acrylic acid-containing solution including a low boiling substance in the range of 0.7–7.5 wt % based on the weight of bottom liquid of absorption column, preferably 0.2–6.7 times the mass flow rate and obtaining an acrylic acid-containing solution including the low boiling substance in the range of 0.75–6.4 wt %, more preferably 0.2–4.8 times the mass flow rate and obtaining an acrylic acid-containing solution including the low boiling substance in the range of 1.2–6.4 wt %. The reason for specifying this range is that the absorbent used in that amount can lower the concentration of the low boiling substance relative to the concentration of acrylic acid and, at the same time, obtain an organic liquid containing acrylic acid at a high concentration. Incidentally, the difference in the amount of the absorbent causes variation in the amount of the low boiling substance to be absorbed for some unclear reason. It may be logically explained, however, by a supposition that the low boiling substance is discharged as the waste gas through the top of the acrylic acid absorption column because it is more gasifiable than acrylic acid in the column and the content of the low boiling substance in the bottoms of the acrylic acid absorption column is lowered in a specific range, with the possibility of the absorbent used in the amount mentioned above being physically entrained in the absorbent for the low boiling substance as a contributory factor.

In addition to the adjustment of the amount of the absorbent to be brought into contact with the reaction gas and the adjustment of the temperature of the absorbent, the conditions for the absorption are so set that the composition of the bottoms has a high acrylic acid concentration and the acrylic acid, a substance liable to form a polymer, is prevented from undergoing polymerization. The items thus set for the accomplishment of this invention include the pressure in the top of the absorption column, the theoretical number of plates of the acrylic acid absorption column, the kind of packings, and the temperature of the top of the column.

For example, as the acrylic acid absorption column, such known columns as a plate column, a packed column, a wetted-wall column, and a spray column may be used. Ordinarily, the plate column or the packed column is preferably used.

The packed column thus used is preferred to have disposed on the upstream side along the flow of the absorbent inside the column a packing having a relatively high efficiency of absorption for acrylic acid and on the downstream side a packing having a relatively low ability to polymerize acrylic acid and/or plates. The term "relatively high (low)" means that a specific packing among other plurality of packings possesses the quality in question at a high level. The expression "a packing having a relatively low ability to polymerize" means that when the acrylic acid absorption column is filled with a plurality of packings, the specific packing has a low ability to form a polymer as compared with the rest of the packings. Usually, the upper part of the acrylic acid absorption column corresponds to the upstream side because it establishes counter-flow contact between the solvent and the acrylic acid-containing gas and the lower part of the acrylic acid absorption column, namely, the direction of entrance for the acrylic acid-containing gas corresponds to the downstream side. In the method of purification according to this invention, the acrylic acid is absorbed at a higher concentration than when the absorption is made by using the conventional high boiling inert hydrophobic organic liquid. The layout of the packings in the column mentioned above is necessary because the acrylic acid is liable to generate a polymer in the column.

The acrylic acid absorption column has packings and plates as articles for inner packaging. In the ordinary column, the gauze type regular packing has the highest efficiency of absorption and is followed sequentially by a sheet type regular packing, an irregular packing, a grid type regular packing, and plates. Even the plates are on a par in the efficiency of absorption with a sheet type regular packing and an irregular packing when they are endowed with high performance. Concerning the ease with which acrylic acid is caused to polymerize, the gauze type regular packing ranks at the top and is followed sequentially by the sheet type regular packing, irregular packing, grid type regular packing, and plates. When the gauze type regular packing is used in an effort to heighten the efficiency of absorption, for example, it entails the problem of polymerization and infeasibilizing lasting operation because it is liable to polymerize a substance under treatment. Conversely, when the grid type regular packing, for example, is used in an effort to prevent polymerization, since it has a low efficiency of absorption, it entails the necessity for unduly increasing the height of the column for the purpose of obtaining a prescribed degree of efficiency. Thus, by using the gauze type regular packing on the upstream side in the flow of the solvent-containing liquid inside the column and at least one member selected from the group consisting of sheet type regular packing, irregular packing, grid type regular packing and plates, particularly the sheet type regular packing, and/or the irregular packing on the downstream side, the prevention of polymerization and the exaltation of the efficiency of absorption are both fulfilled to ensure a lasting stable operation.

The commercial products of the gauze type regular packing include sluzer Packing (made by Sumitomo Heavy Industries Co., Ltd.), Technopack (made by Mitsui & Co., Ltd.), and MC Pack (made by Mitsubishi Chemical Engineering Co.), those of the sheet type regular packing include MELLAPAK (made by Sumitomo Heavy Industries Co., Ltd.), Technopack (made by Mitsui & Co., Ltd.), MC Pack (made by Mitsubishi Chemical Engineering Co.), those of the grid type regular packing include Flexy Gride (made by KOCH ENGINEERING COMPANY INC), those of the irregular packing include Raschig Ring, Pauling, Cascade Mini Ring (made by Dodwell & Co., Ltd.) and IMTP (made by Norton Chemical Process Products Corp), and those of the plates include sieve tray, bulb tray, bubble cap tray, baffle tray, dual flow tray, super flack tray, ripple tray, and jet tray, for example.

Among other irregular packings, the Casecade Mini Ring and IMTP which are flat fillings proves particularly advantageous because they are capable of filling a space as closely as a regular packing, because they excel in the ability to prevent polymerization, and they have a high efficiency of absorption.

Further, the top of the acrylic acid absorption column is ordinarily operated at a slightly higher pressure. The column top pressure (gauge pressure) is preferably in the range of 5 kPa–30 kPa, more preferably in the range of 10–20 kPa. The reason for the use of this pressure is that the amount of the low boiling substance in the bottoms of the acrylic acid absorption column can be decreased by discharging the low boiling substance through the top of the column.

The acrylic acid-containing gas obtained in consequence of the catalytic gas phase oxidation is introduced into the acrylic acid absorption column through the lower part thereof. Part of the acrylic acid solution drawn through the bottom part of the column is forwarded to the subsequent step of purification and the remainder of the solution is cooled in an external cooling device (22). The cooled solution is introduced into the acrylic acid absorption column and brought into counter-flow contact with the gas preferably to condense and cool the gas. Optionally, the liquid other than the bottoms of the column, when necessary, is drawn and cooled and the cooled liquid is introduced into the acrylic acid absorption column. Otherwise, the absorbent may be cooled and then introduced into the acrylic acid absorption column.

The external cooling device (22) does not need to be particularly restricted but is only required to be a heat exchanger which is capable of indirectly cooling a liquid. As concrete examples of the external cooling device, such known heat exchangers as a shell-and-tube type heat exchanger, a double-pipe heat exchanger, a spiral type heat exchanger, and a plate type heat exchanger may be cited. This cooling is effected till the temperature at a certain point inside the acrylic acid absorption column reaches a prescribed level. Generally, the cooling is controlled by the temperature of the top of the column.

Further, when the cooled liquid obtained in the cooling device is circulated to the acrylic acid absorption column, the position of this acrylic acid absorption column is generally 1–10 theoretical plates, preferably 1–5 theoretical plates, and further preferably 2–4 theoretical plates, above the position for the drawing of liquid.

In the case of the packed column, the distribution of the liquid flowing down the interior of the column forms the most important factor with respect to the efficiency of absorption. When the packed filler has a large height, it is commendable for the purpose of preventing the liquid from producing a drift current to have a liquid distributing devices disposed not only at the inlet for the liquid but also on the packed layer at least one point halfway along the length of the column. Generally, the pipe orifice mode or the gas riser liquid hole drip mode is adopted for the liquid distributing device. Since either of these modes is so adapted as to apply a certain degree of pressure in the liquid hole and cause the liquid to flow uniformly through a multiplicity of orifices, the orifices have such a small diameter as to entail the possibility of clogging the orifices frequently with a polymer, for example, lowering the efficiency of absorption, and forcing the operation to be suspended. By using the liquid distributing device of the overflow mode, therefore, it is made possible to keep the efficiency of absorption intact and ensure the operation to continue for a long time. The liquid distributing device of the overflow mode, for example, is adapted to have numerous notches cut in the upper end of the liquid distribution tube and allow the liquid to be distributed as it overflows the notches. It is effectively used without reference to the shape.

This invention separates the low boiling substance by distilling the high boiling inert-hydrophobic organic liquid containing the reaction gas component to be obtained by the reaction of catalytic gas phase oxidation, namely the organic liquid containing a high concentration of acrylic acid. As the light ends cut column (30), any of the known columns such as, for example, a plate column, a packed column, a wetted-wall column, and a spray column may be used. Similarly to the acrylic acid absorption column mentioned above, this light ends cut column (30) is generally preferred to be a plate column or a packed column.

To the light ends cut column (30), the organic liquid containing acrylic acid at a high concentration of acrylic acid (hereinafter referred to as "acrylic acid-containing organic liquid") is supplied so as to effect removal of the low boiling substance entrained in the liquid. The low boiling substances possibly entrained by the liquid include formic acid, acetic acid, acrolein, formaldehyde, acetaldehyde, and water, for example. The temperature at which the acrylic acid-containing organic liquid is supplied to the separation column (30) is preferably in the range of 50–90° C., and more preferably in the range of 60–80° C.

For the separation in the light ends cut column (30), the conditions adopted by the known methods of separation may be employed. For, this invention has originated in the discovery that the efficiency of separation of the low boiling substances can be exalted by using the organic liquid containing acrylic acid at a concentration which has never been used in the art. Incidentally, the preferred theoretical plate number of the separation column (30) is in the range of 10–20.

When the flow rate of the distillate emanating from the top of the separation column (30) is set at a level in the range of 1.0–2.0 times, preferably in the range of 1.2–1.8 times, and particularly in the range of 1.2–1.6 times, the flow rate of the low boiling substance in the liquid being supplied, for example, the reflux ratio from the condenser (31) attached to the separation column (30) is in the range of 1.0–20.0, preferably in the range of 3.0–10.0, and particularly in the range of 3.0–6.0. If the flow rate of the distillate falls short of 1.0 times the flow rate of the low boiling substance, the shortage will be at a disadvantage in inducing effusion of the surplus low boiling substance through the bottom of the column and heightening the concentration of the low boiling substance in the product without reference to the efficiency of separation of the separation column. Conversely, if the flow rate exceeds 2.0 times the flow rate of the low boiling substance, the excess will be at a disadvantage in not only requiring an unduly large energy but also heightening the possibility of entailing polymerization in the neighborhood of the top of the column. The pressure of the column at the top (absolute pressure) is set at a level in the range of 3–30 kPa, preferably in the range of 3–15 kPa, and particularly in the range of 5–13 kPa. If this pressure falls short of 3 kPa, the shortage will be at a disadvantage in not merely entailing an undue addition to the size of the vacuum device but also lowering the temperature of the top of the column and consequently requiring the condenser to have an increased size. Conversely, if this pressure exceeds 30 kPa, the excess will be at a disadvantage in entailing generation of a polymer in addition to heightening the temperature of the bottom of the column and adding to the size of the reboiler. Since the distillate from the light ends cut column still contains acrylic acid at a fairly high concentration, it is advantageous to circulate the distillate to the acrylic acid absorption column (20) and increase the ratio of recovery of acrylic acid. The distillate may be circulated to the acrylic acid absorption column after the low boiling substance contained therein has been separated and removed or it may be circulated to the acrylic acid absorption column (20) without undergoing this treatment. Particularly when the distillate from the condenser is circulated to the acrylic acid absorption column (20), the position of the acrylic acid absorption column (20) is preferred to intervene between the inlet for resupplying the acrylic acid-containing solution cooled in the cooling device (22) into the acrylic acid absorption column (20) and the inlet for injecting the absorbent.

It is commendable to have part of the acrylic acid solution drawn from the bottom of the column supplied to the light ends cut column (30) and the remainder thereof heated in the reboiler (32) and circulated again to the light ends cut column (30). The reboiler (32) is preferred to be supplied with molecular oxygen. This supply of the molecular oxygen may be effected by means of air bubbling or by being directly admixed with acrylic acid. When the molecular oxygen is delivered in the gaseous state from the bottom of the distillation column and/or the reboiler, the device for air bubbling can be easily incorporated into the process of production. Preferably, the molecular oxygen is introduced into the vapor of acrylic acid in an amount approximately in the range of 0.1–1.0 vol. % based on the volume of the vapor.

It is commendable for the purpose of preventing acrylic acid from undergoing the detrimental phenomenon of polymerization in the light ends cut column (30) to add any of the known polymerization inhibitors such as, for example, methoquinone, manganese acetate, nitrosophenol, cupferron, N-oxyl compound, copper dibutylthiocarbamate, phenothiazine, or hydroquinone suitably to the column. Such a polymerization inhibitor can be supplied through the top of the column. For the same purpose, a molecular oxygen-containing gas may be blown into the column through the bottom thereof.

It is commendable for the bottoms in the light ends cut column (30) to be supplied to the heavy ends cut column (40) and separated of the high boiling substance to effect purification of the acrylic acid entrained therein.

As the heavy ends cut column (40), any of the known columns such as, for example, a plate column, a packed column, a wetted-wall column, or a spray column may be used. Similarly to the light ends cut column (30) mentioned above, this heavy ends cut column (40) is generally preferred to be a plate column or a packed column. The theoretical plate number of this column is preferred to be in the range of 5–20.

The distillation in the heavy ends cut column (40) can be performed under any of the known conditions of distillation. The pressure in the top of the column (absolute pressure), for example, is in the range of 3–30 kPa, preferably in the range of 3–15 kPa, and particularly in the range of 5–13 kPa. The amount of the distillate can be suitably fixed in accordance with the tolerance of the high boiling impurity in the product. The ratio of reflux is generally in the range of 0.5–5.

Similarly to the light ends cut column (30) mentioned above, the heavy ends cut column (40) prefers suitable addition thereto of any of the known polymerization inhibitors such as, for example, methoquinone, manganese acetate, nitrosophenol, cupferron, N-oxyl compound, copper dibuylthiocarbamate, phenothiazine, or hydroquinone for the purpose of preventing acrylic acid from undergoing the detrimental phenomenon of polymerization. Such a polymerization inhibitor can be supplied through the top of the column. For the same purpose, a molecular oxygen-containing gas may be blown into the column through the bottom thereof.

Incidentally, the heavy ends cut column (40) permits part of the bottoms therein to be discarded as an organic substance-containing waste oil. It is, however, permissible to re-purify the high boiling solvent and reclaim an absorbent for use in the acrylic acid absorption column (20). It is commendable for the remainder thereof to be heated in the reboiler (42) and circulated again to the heavy ends cut column (40). Incidentally, the reboiler (42) is supplied with a molecular oxygen. The supply of this molecular oxygen may be effected by means of air bubbling or by being directly admixed with the feed liquid. When the molecular oxygen is delivered in the gaseous state from the heavy ends cut column (40) or the reboiler (42), the device for air bubbling can be incorporated in the process of production. Preferably, the molecular oxygen is introduced into the vapor of acrylic acid in an amount approximately in the range of 0.1–1.0 vol. % based on the volume of the vapor.

The acrylic acid is distilled through the top of the heavy ends cut column (40). Generally the purity of this acrylic acid in the distillate is in the range of 99.5–99.9 weight %.

EXPERIMENTS

Now, this invention will be described more specifically below with reference to working examples.

Example 1

In accordance with the process depicted in FIG. 2, acrylic acid was purified through the step for preparation of an acrylic acid-containing gas by the reaction of catalytic gas phase oxidation and the subsequent use of an acrylic acid absorption column, a light ends cut column, and a heavy ends cut column.

(1) By the reaction of catalytic gas phase oxidation, an acrylic acid-containing gas composed of 7.15 vol. % of acrylic acid, 14.6 vol. % of low boiling substances (total of formic acid, acetic acid, acrolein, formaldehyde, acetaldehyde, and water), 0.15 vol. % of high boiling substances (total of furfural and maleic anhydride), and 78.1 vol. % of uncondensing gas (total of nitrogen, oxygen, propylene, propane, carbon monoxide, and carbon dioxide) was obtained.

(2) The acrylic acid-containing gas was supplied to the acrylic acid absorption column. The temperature at which the acrylic acid-containing gas was supplied was 150° C. The acrylic acid absorption column measured 54.9 mm in diameter. The column was charged with three beds of sulzer DX each measuring 1100 mm in length. Here, an absorbent consisting of 73.5 weight % of diphenyl ether and 26.5 weight % of diphenyl and containing 4-hydroxy-2,2,6,6-tetramethyl piperidinoxyl as a polymerization inhibitor at a ratio of 100 weight ppm relative to the amount of acrylic acid in the reaction gas was used to effect absorption of acrylic acid. The acrylic acid-containing gas was supplied to the acrylic acid absorption column at a feed rate of 8.14 Nm3/h and the absorbent at a feed rate of 4.3 kg/h (2.3 times the mass flow rate of the acrylic acid). When the absorption of acrylic acid was effected by setting the pressure in the top of the column at 11.7 kPa (gauge pressure) and the temperature in the top of the column at 47.7° C., absorbing coefficient of acrylic acid was 98.1 weight %, the concentration of acrylic acid in the bottoms of the column was 29.6 weight %, and the concentration of the low boiling substance relative to the acrylic acid was 7.0 weight %.

(3) The bottoms of the column were supplied to the light ends cut column. This distillation column was an oldershaw using 28 plates and was operated at a column top pressure of 10 kPa (absolute pressure), a reflux ratio of 4, and a distillate rate of 170 g/h to expel the low boiling substance by distillation. The composition of the bottoms of the distillation column was such that the low boiling substance concentration relative to acrylic acid was 600 weight ppm.

(4) Then, the bottoms of the column were supplied to the heavy ends cut column. This distillation column was an oldershaw using 22 plates and was operated at a column top pressure of 10 kPa (absolute pressure), a reflux ratio of 1, and a distillate rate of 1840 g/h to expel the high boiling substance by distillation. The low boiling substance concentration in the distillate from the distillation column was 600 weight ppm.

Concentration of acrylic acid (AA) in reaction gas, amount of absorbent to absorption column, top temperature of the absorption column, ratio of amount of absorbent/gas, concentration of acrylic acid in bottom liquid in absorption column, concentration of a the low boiling substance liquid (LB) in absorption column, LB/AA ratio in absorption column, LB/AA ratio in distillation column, ratio of LB separation, concentration of LB in product, absorbing coefficient of acrylic acid in each Example and Comparative Example are shown in the table 2.

Example 2

(1) An acrylic acid-containing gas having the same composition as in Example 1 was prepared.

(2) Then, the acrylic acid-containing gas was supplied to the acrylic acid absorption column. The acrylic acid absorption column and the absorbent used herein were the same as those used in Example 1. The temperature at which the acrylic acid-containing gas was supplied was 150° C. similarly in Example 1 and the feed rate of the gas to the acrylic acid absorption column was 8.14 Nm3/h. When the absorption of acrylic acid was effected by setting the flow rate of the absorbent at 1.1 kg/h (0.6 times the mass flow rate of the acrylic acid), the column top pressure at 11.7 kPa (gauge pressure), and the column top temperature at 41.2° C., the absorbing coefficient of acrylic acid was 98.1 weight %, the concentration of acrylic acid in the bottoms was 59.9 weight %, and the concentration of the low boiling substance relative to acrylic acid was 7.2 weight %.

(3) The bottoms of the column were supplied to the same light ends cut column as used in Example 1. The column was operated at a column top pressure of 10 kPa (absolute pressure), a reflux ratio of 4, and a distillate rate of 170 g/h to expel the low boiling substance by distillation. The composition of the bottoms in the distillation column was such that the concentration of the low boiling substance relative to acrylic acid was 360 weight ppm.

(4) Then, the bottoms of the column were supplied to the same heavy ends cut column as used in Example 1. This column was operated at a column top pressure of 10 kPa (absolute pressure), a reflux ratio of 1, and a distillate rate of 1840 g/h to expel the high boiling substance by distillation. The concentration of the low boiling substance in the distillate from the distillation column was 360 weight ppm.

Example 3

(1) An acrylic acid-containing gas having the same composition as in Example 1 was prepared.

(2) Then, the acrylic acid-containing gas was supplied to the acrylic acid absorption column. The acrylic acid absorption column and the absorbent used herein were the same as those in Example 1. The temperature at which the acrylic acid-containing gas was supplied was 150° C. similarly in Example 1 and the feed rate of this gas to the acrylic acid absorption column was 8.14 Nm3/h. When the absorption of acrylic acid was effected by setting the flow rate of the absorbent at 7.5 kg/h (4.0 times the mass flow rate of the acrylic acid), the column top pressure at 11.7 kPa (gauge pressure), and the column top temperature at 53.8° C., the absorbing coefficient of acrylic acid was 98.1 weight %, the concentration of acrylic acid in the bottoms was 19.7 weight %, and the concentration of the low boiling substance relative to acrylic acid was 7.3 weight %.

(3) The bottoms were supplied to the same light ends cut column as used in Example 1. This column was operated at a column top pressure of 10 kPa (absolute pressure), a reflux ratio of 4, and a distillate rate of 170 g/h to expel the low boiling substance by distillation. The composition of the bottoms in the distillation column was such that the concentration of the low boiling substance relative to acrylic acid was 1360 weight ppm.

(4) Then, the bottoms of the column were supplied to the same heavy ends cut column as used in Example 1. The column was operated at a column top pressure of 10 kPa (absolute pressure), a reflux ratio of 1, and a distillate rate of 1840 g/h to expel the high boiling substance by distillation. The concentration of the low boiling substance in the distillate from this distillation column was 1370 weight ppm.

Example 4

(1) An acrylic acid-containing gas having the same composition as in Example 1 was prepared.

(2) Then, this acrylic acid-containing gas was supplied to the acrylic acid absorption column. The acrylic acid absorption column and the absorbent used herein were the same as those in Example 1. The temperature at which the acrylic acid-containing gas was supplied was 150° C. similarly in Example 1 and the feed rate of the gas to the acrylic acid absorption column was 8.14 Nm3/h. When the absorption of acrylic acid was effected at an absorbent flow rate of 0.6 kg/h (0.3 times the mass flow rate of the acrylic acid), a column top pressure at 11.7 kPa (gauge pressure), and a column top temperature of 40.3° C., the absorbing coefficient of acrylic acid was 98.1 weight %, the concentration of acrylic acid in the bottoms of the column was 68.9 weight %, and the concentration of the low boiling substance relative to acrylic acid was 8.0 weight %.

(3) The bottoms were supplied to the same light ends cut column as used in Example 1. This column was operated at a column top pressure of 10 kPa (absolute pressure), a reflux ratio of 4, and a distillate rate of 170 g/h to expel the low boiling substance by distillation. The composition of the bottoms in the distillation column was such that the concentration of the low boiling substance relative to acrylic acid was 580 weight ppm.

(4) Then, the bottoms of the column were supplied to the same heavy ends cut column as used in Example 1. The column was operated at a column top pressure of 10 kPa (absolute pressure), a reflux ratio of 1, and a distillate rate of 1840 g/h to expel the high boiling substance by distillation. The concentration of the low boiling substance in the distillate from this distillation column was 580 weight ppm.

Example 5

(1) An acrylic acid-containing gas having the same composition as in Example 1 was prepared.

(2) Then, this acrylic acid-containing gas was supplied to the acrylic acid absorption column. The acrylic acid absorption column and the absorbent used herein were the same as those in Example 1. The temperature at which the acrylic acid-containing gas was supplied was 150° C. similarly in Example 1 and the flow rate of the gas to the acrylic acid absorption column was 8.14 Nm3/h. When the absorption of acrylic acid was effected at an absorbent flow rate of 0.4 kg/h (0.2 times the mass flow rate of the acrylic acid), a column top pressure at 11.7 kPa (gauge pressure), and a column top temperature of 39.8° C., the absorbing coefficient of acrylic acid was 98.1 weight %, the concentration of acrylic acid in the bottoms of the column was 74.4 weight %, and the concentration of the low boiling substance relative to acrylic acid was 8.6 weight %.

(3) The bottoms were supplied to the same light ends cut column as used in Example 1. This column was operated at a column top pressure of 10 kPa (absolute pressure), a reflux ratio of 4, and a distillate rate of 170 g/h to expel the low boiling substance by distillation. The composition of the bottoms in the distillation column was such that the concentration of the low boiling substance relative to acrylic acid was 1340 weight ppm.

(4) Then, the bottoms of the column were supplied to the same heavy ends cut column as used in Example 1. The column was operated at a column top pressure of 10 kPa (absolute pressure), a reflux ratio of 1, and a distillate rate of 1840 g/h to expel the high boiling substance by distillation. The concentration of the low boiling substance in the distillate from this distillation column was 1340 weight ppm.

Example 6

(1) An acrylic acid-containing gas was prepared by the reaction of catalytic gas phase oxidation. This gas was composed of 5.35 vol. % of acrylic acid, 12.25 vol. % of low boiling substances (total of formic acid, acetic acid, acrolein, formaldehyde, acetaldehyde, and water), 0.1 vol. % of high boiling substances (total of furfural and maleic anhydride), and 82.3 vol. % of uncondensing gas (total of nitrogen, oxygen, propylene, propane, carbon monoxide, and carbon dioxide).

(2) Then, this acrylic acid-containing gas was supplied to the acrylic acid absorption column. The acrylic acid absorption column and the absorbent used herein were the same as those in Example 1. The temperature at which the acrylic acid-containing gas was supplied was 150° C. similarly in Example 1. When the absorption of acrylic acid was effected by setting the feed rate of the gas to the acrylic acid absorption column at 10.92 Nm3/h, the absorbent feed rate at 4.3 kg/h (2.3 times the mass flow rate of the acrylic acid), the column top pressure at 11.7 kPa (gauge pressure), and the column top temperature at 42.2° C., the absorbing coefficient of acrylic acid was 98.1 weight %, the concentration of acrylic acid in the bottoms of the column was 29.6 weight %, and the concentration of the low boiling substance relative to acrylic acid was 6.9 weight %.

(3) The bottoms were supplied to the same light ends cut column as used in Example 1. This column was operated at a column top pressure of 10 kPa (absolute pressure), a reflux ratio of 4, and a distillate rate of 170 g/h to expel the low boiling substance by distillation. The composition of the bottoms in the distillation column was such that the concentration of the low boiling substance relative to acrylic acid was 520 weight ppm.

(4) Then, the bottoms of the column were supplied to the same heavy ends cut column as used in Example 1. The column was operated at a column top pressure of 10 kPa (absolute pressure), a reflux ratio of 1, and a distillate rate of 1840 g/h to expel the high boiling substance by distillation. The concentration of the low boiling substance in the distillate from this distillation column was 520 weight ppm.

Example 7

(1) An acrylic acid-containing gas was prepared by the reaction of catalytic gas phase oxidation. This gas was composed of 8.55 vol. % of acrylic acid, 16.45 vol. % of low boiling substances (total of formic acid, acetic acid, acrolein, formaldehyde, acetaldehyde, and water), 0.15 vol. % of high boiling substances (total of furfural and maleic anhydride), and 74.85 vol. % of uncondensing gas (total of nitrogen, oxygen, propylene, propane, carbon monoxide, and carbon dioxide).

(2) Then, this acrylic acid-containing gas was supplied to the acrylic acid absorption column. The acrylic acid absorption column and the absorbent used herein were the same as those in Example 1. The temperature at which the acrylic acid-containing gas was supplied was 150° C. similarly in Example 1. When the absorption of acrylic acid was effected by setting the feed rate of the gas to the acrylic acid absorption column at 6.82 Nm3/h, the absorbent feed rate at 4.3 kg/h (2.3 times the mass flow rate of the acrylic acid), the column top pressure at 11.7 kPa (gauge pressure), and the column top temperature at 51.5° C., the absorbing coefficient of acrylic acid was 98.1 weight %, the concentration of acrylic acid in the bottoms of the column was 7.1 weight %, and the concentration of the low boiling substance relative to acrylic acid was 29.6 weight %.

(3) The bottoms were supplied to the same light ends cut column as used in Example 1. This column was operated at a column top pressure of 10 kPa (absolute pressure), a reflux ratio of 4, and a distillate rate of 170 g/h to expel the low boiling substance by distillation. The composition of the bottoms in the distillation column was such that the concentration of the low boiling substance relative to acrylic acid was 670 weight ppm.

(4) Then, the bottoms of the column were supplied to the same heavy ends cut column as used in Example 1. The column was operated at a column top pressure of 10 kPa (absolute pressure), a reflux ratio of 1, and a distillate rate of 1840 g/h to expel the high boiling substance by distillation. The concentration of the low boiling substance in the distillate from this distillation column was 670 weight ppm.

Example 8

(1) An acrylic acid-containing gas having the same composition as in Example 1 was prepared.

(2) Then, this acrylic acid-containing gas was supplied to the acrylic acid absorption column. The acrylic acid absorption column and the absorbent used herein were the same as those in Example 1. The temperature at which the acrylic acid-containing gas was supplied was 150° C. similarly in Example 1 and the feed rate of the gas to the acrylic acid absorption column was 8.14 Nm3/h. When the absorption of acrylic acid was effected by setting the feed rate of the absorbent at 10.5 kg/h (5.6 times the mass flow rate of the acrylic acid), the column top pressure at 11.7 kPa (gauge pressure), and the column top temperature at 59.9° C., the absorbing coefficient of acrylic acid was 97.9 weight %, the concentration of acrylic acid in the bottoms of the column was 15.0 weight %, and the concentration of the low boiling substance relative to acrylic acid was 7.5 weight %.

(3) The bottoms were supplied to the same light ends cut column as used in Example 1. This column was operated at a column top pressure of 10 kPa (absolute pressure), a reflux ratio of 4, and a distillate rate of 170 g/h to expel the low boiling substance by distillation. The composition of the bottoms in the distillation column was such that the concentration of the low boiling substance relative to acrylic acid was 2480 weight ppm.

(4) Then, the bottoms of the column were supplied to the same heavy ends cut column as used in Example 1. The column was operated at a column top pressure of 10 kPa (absolute pressure), a reflux ratio of 1, and a distillate rate of 1840 g/h to expel the high boiling substance by distillation. The concentration of the low boiling substance in the distillate from this distillation column was 2490 weight ppm.

Comparative Example 1

(1) An acrylic acid-containing gas having the same composition as in Example 1 was prepared.

(2) Then, this acrylic acid-containing gas was supplied to the acrylic acid absorption column. The acrylic acid absorption column and the absorbent used herein were the same as those in Example 1. The temperature at which the acrylic acid-containing gas was supplied was 150° C. similarly in Example 1 and the feed volume of the gas to the acrylic acid absorption column was 8.14 Nm3/h. When the absorption of acrylic acid was effected by setting the feed rate of the absorbent at 0.2 kg/h (0.1 times the mass flow rate of the acrylic acid), the column top pressure at 11.7 kPa (gauge pressure), and the column top temperature at 39.2° C., the absorbing coefficient of acrylic acid was 97.6 weight %, the concentration of acrylic acid in the bottoms of the column was 87.1 weight %, and the concentration of the low boiling substance relative to acrylic acid was 9.3 weight %.

(3) The bottoms were supplied to the same light ends cut column as used in Example 1. This column was operated at a column top pressure of 10 kPa (absolute pressure), a reflux ratio of 4, and a distillate rate of 170 g/h to expel the low boiling substance by distillation. The composition of the bottoms in the distillation column was such that the concentration of the low boiling substance relative to acrylic acid was 5400 weight ppm.

(4) Then, the bottoms of the column were supplied to the same heavy ends cut column as used in Example 1. The column was operated at a column top pressure of 10 kPa (absolute pressure), a reflux ratio of 1, and a distillate rate of 1840 g/h to expel the high boiling substance by distillation. The concentration of the low boiling substance in the distillate from this distillation column was 5380 weight ppm.

Examples 9–16

(1) An acrylic acid-containing gas having the same composition as in Example 1 was prepared.

(2) Then, the acrylic acid-containing gas was supplied to the acrylic acid absorption column. The acrylic acid absorption column and the absorbent used herein were the same as those used in Example 1. The temperature at which the acrylic acid-containing gas was supplied was 150° C. similarly in Example 1 and the feed rate of the gas to the acrylic acid absorption column was 8.14 Nm3/h. In each example, acrylic acid in the gas was absorbed in the absorbent as being adjusted the flow rate of the absorbent and the column top temperature in the values shown table 2 and the column top pressure at 11.7 kPa (gauge pressure).

(3) The bottoms of the column were supplied to the same light ends cut column as used in Example 1. The column was operated at a column top pressure of 10 kPa (absolute pressure), a reflux ratio of 4, and a distillate rate of 170 g/h to expal the low boiling substance by distillation.

(4) Then, the bottoms of the column were supplied to the same heavy ends cut column as used in Example 1. This column was operated at a column top pressure of 10 kPa (absolute pressure), a reflux ratio of 1, and a distillate rate of 1840 g/h to expel the high boiling substance by distillation.

Examples 17 and 18

(1) An acrylic acid-containing gas was prepared by the reaction of catalytic gas phase oxidation. This gas was composed of 5.35 vol. % of acrylic acid, 12.25 vol. % of low boiling substances (total of formic acid, acetic acid, acrolein, formaldehyde, acetaldehyde, and water), 0.1 vol. % of high boiling substances (total of furfural and maleic anhydride), and 82.3 vol. % of uncondensing gas (total of nitrogen, oxygen, propylene, propane, carbon monoxide, and carbon dioxide).

(2) Then, the acrylic acid-containing gas was supplied to the acrylic acid absorption column. The acrylic acid absorption column and the absorbent used herein were the same as those used in Example 1. The temperature at which the acrylic acid-containing gas was supplied was 150° C. similarly in Example 1 and the feed rate of the gas to the acrylic acid absorption column was 8.14 Nm3/h. In each example, acrylic acid in the gas was absorbed in the absorbent as being adjusted the flow rate of the absorbent and the column top temperature in the values shown table 2 and the column top pressure at 11.7 kPa (gauge pressure).

(3) The bottoms of the column were supplied to the same light ends cut column as used in Example 1. The column was operated at a column top pressure of 10 kPa (absolute pressure), a reflux ratio of 4, and a distillate rate of 170 g/h to expal the low boiling substance by distillation.

(4) Then, the bottoms of the column were supplied to the same heavy ends cut column as used in Example 1. This column was operated at a column top pressure of 10 kPa (absolute pressure), a reflux ratio of 1, and a distillate rate of 1840 g/h to expel the high boiling substance by distillation.

Comparative Example 2

(1) An acrylic acid-containing gas having the same composition as in Example 17 was prepared.

(2) Then, the acrylic acid-containing gas was supplied to the acrylic acid absorption column. The acrylic acid absorption column and the absorbent used herein were the same as those used in Example 1. The temperature at which the acrylic acid-containing gas was supplied was 150° C. similarly in Example 1 and the feed rate of the gas to the acrylic acid absorption column was 8.14 Nm3/h. In the comparative example 2, acrylic acid in the gas was absorbed in the absorbent as being adjusted the flow rate of the absorbent and the column top temperature in the values shown table 2 and the column top pressure at 11.7 kPa (gauge pressure).

(3) The bottoms of the column were supplied to the same light ends cut column as used in Example 1. The column was operated at a column top pressure of 10 kPa (absolute pressure), a reflux ratio of 4, and a distillate rate of 170 g/h to expal the low boiling substance by distillation.

(4) Then, the bottoms of the column were supplied to the same heavy ends cut column as used in Example 1. This column was operated at a column top pressure of 10 kPa (absolute pressure), a reflux ratio of 1, and a distillate rate of 1840 g/h to expel the high boiling substance by distillation.

TABLE 2

| | | Absorption column | | | Bottoms liquid of acrylic acid absorption column | | | Bottoms liquid of light ends cut column | | | |
|---|---|---|---|---|---|---|---|---|---|---|---|
| | AA conc. in reaction gas (vol %) | amount of absorbent (kg/h) | Top temp. (□) | Amount of absorbent/ gas | AA conc. (w□. %) | LB conc. (w□. %) | LB/AA ratio (w□. %) (X) | LB/AA ratio (wt ppm) (Y) | Ratio of LB separation (X − Y)/X | LB conc. (w□. %) | Effect of absorption |
| Ex. 9 | 7.15 | 12.5 | 62.7 | 6.7 | 13.1 | 1.00 | 7.6 | 3380 | 0.956 | 3410 | 97.8 |
| Ex. 10 | 7.15 | 11.4 | 61.3 | 6.1 | 14.1 | 1.07 | 7.6 | 2860 | 0.962 | 2880 | 97.9 |
| Ex. 8 | 7.15 | 10.5 | 59.9 | 5.6 | 15.0 | 1.13 | 7.5 | 2480 | 0.967 | 2490 | 97.9 |
| Ex. 11 | 7.15 | 9.0 | 56.8 | 4.8 | 17.0 | 1.26 | 7.4 | 1880 | 0.975 | 1890 | 98.0 |
| Ex. 3 | 7.15 | 7.5 | 53.8 | 4.0 | 19.7 | 1.44 | 7.3 | 1360 | 0.982 | 1370 | 98.1 |
| Ex. 1 | 7.15 | 4.3 | 47.7 | 2.3 | 29.6 | 2.07 | 7.0 | 600 | 0.992 | 600 | 98.1 |
| Ex. 12 | 7.15 | 2.6 | 44.2 | 1.4 | 40.6 | 2.80 | 6.9 | 390 | 0.995 | 390 | 98.1 |
| Ex. 13 | 7.15 | 1.7 | 42.6 | 0.9 | 49.8 | 3.44 | 6.9 | 330 | 0.995 | 330 | 98.1 |
| Ex. 14 | 7.15 | 1.5 | 42.1 | 0.8 | 52.8 | 3.70 | 7.0 | 330 | 0.995 | 330 | 98.1 |
| Ex. 15 | 7.15 | 1.3 | 41.6 | 0.7 | 56.1 | 3.98 | 7.1 | 340 | 0.995 | 340 | 98.1 |
| Ex. 2 | 7.15 | 1.1 | 41.2 | 0.6 | 59.9 | 4.31 | 7.2 | 360 | 0.995 | 360 | 98.1 |
| Ex. 16 | 7.15 | 0.9 | 40.7 | 0.5 | 64.1 | 4.81 | 7.5 | 410 | 0.995 | 410 | 98.1 |
| Ex. 4 | 7.15 | 0.6 | 40.3 | 0.3 | 68.9 | 5.51 | 8.0 | 580 | 0.993 | 580 | 98.1 |
| Ex. 5 | 7.15 | 0.4 | 39.8 | 0.2 | 74.4 | 6.40 | 8.6 | 1340 | 0.985 | 1340 | 98.1 |
| C. Ex. 1 | 7.15 | 0.2 | 39.2 | 0.1 | 87.1 | 8.10 | 9.3 | 5400 | 0.942 | 5380 | 97.6 |
| Ex. 17 | 7.56 | 11.1 | 59.0 | 5.6 | 15.4 | 0.79 | 5.1 | 3410 | 0.933 | 3430 | 97.9 |
| Ex. 18 | 7.56 | 12.1 | 60.8 | 6.1 | 14.4 | 0.75 | 5.2 | 3730 | 0.928 | 3750 | 97.8 |
| C. Ex. 2 | 7.56 | 15.8 | 64.8 | 8.0 | 11.5 | 0.62 | 5.4 | 4990 | 0.908 | 5060 | 97.7 |
| Ex. 6 | 5.35 | 4.3 | 42.2 | 2.3 | 29.6 | 2.05 | 6.9 | 520 | 0.993 | 520 | 98.1 |
| Ex. 7 | 8.55 | 4.3 | 51.5 | 2.3 | 29.6 | 2.10 | 7.1 | 670 | 0.991 | 670 | 98.1 |

What is claimed is:

1. A method for absorbing acrylic acid by supplying an acrylic acid-containing reaction gas component obtained by the reaction of catalytic gas phase oxidation to an acrylic acid absorption column and advancing a high boiling inert hydrophobic organic liquid into counter-flow contact with said reaction gas in said acrylic acid absorption column with the mass flow rate of the organic liquid fixed in the range of 0.2–7.0 times the mass flow rate of the acrylic acid in the reaction gas thereby absorbing acrylic acid in said organic liquid and obtaining an acrylic acid-containing solution including a low boiling substance in the range of 0.7–7.5 wt % based on the weight of bottom liquid of absorption column.

2. A method according to claim 1, wherein the temperature of the top of said acrylic acid absorption column is lowered to a level in the range of 20–70° C.

3. A method according to claim 1, wherein the concentration of acrylic acid in the reaction gas obtained by the reaction of catalytic gas phase oxidation is in the range of 3–9 vol. %.

4. A method according to claim 1, wherein said organic liquid supplied for said absorption contains at least one member selected from the group consisting of N-oxyl compounds, phenol compounds, manganese salts, copper salts of dialkyl dithiocarbamic acid, nitroso compounds and amine compounds, or contains said one or more members plus phenothiazine.

5. A method for purifying acrylic acid, comprising the steps of:

absorbing acrylic acid by supplying an acrylic acid-containing reaction gas component obtained by the reaction of catalytic gas phase oxidation to an acrylic acid absorption column and advancing a high boiling inert hydrophobic organic liquid into counter-flow contact with the reaction gas in said acrylic acid absorption column with the mass flow rate of the organic liquid fixed within the range of 0.2 to 7.0 times the mass flow rate of the acrylic acid in the reaction gas thereby absorbing acrylic acid in the organic liquid and obtaining an acrylic acid-containing solution including a low boiling substance in the range of 0.7–7.5 wt % based on the weight of bottom liquid of absorption column; and purifying said acrylic acid-containing organic solution.

* * * * *